United States Patent [19]

Cort

[11] 4,278,595

[45] Jul. 14, 1981

[54] ORALLY ACTIVE MIF ANALOGS WITH AN EFFECT ON THE CENTRAL NERVOUS SYSTEM

[75] Inventor: Joseph H. Cort, New York, N.Y.

[73] Assignee: Vega Laboratories, Inc., Tucson, Ariz.

[21] Appl. No.: 102,149

[22] Filed: Dec. 10, 1979

[51] Int. Cl.$^3$ .................... C07C 103/52; A61K 37/00
[52] U.S. Cl. .............................. 260/112.5 R; 424/177
[58] Field of Search .................. 424/177; 260/112.5 R

[56] References Cited

PUBLICATIONS

S. Bojusz, et al., Acta Biochem. et. Biophys. Acad. Sci Hung. vol. II (1), pp. 305-309, (1976).
Walker, et al., Science 196, (1977), 85-87.
Pert, et al., Science 194, (1976), 330-332.

*Primary Examiner*—Delbert R. Phillips
*Attorney, Agent, or Firm*—Kenyon & Kenyon

[57] ABSTRACT

Tripeptide MIF analogs represented by the formula X—D—Leu—Gly—NR$^1$R$^2$ wherein X is Pro or pGlu, and each of R$^1$ and R$^2$, when taken separately, is hydrogen or lower alkyl, are useful in the treatment of disorders of the central nervous system.

5 Claims, No Drawings

ORALLY ACTIVE MIF ANALOGS WITH AN EFFECT ON THE CENTRAL NERVOUS SYSTEM

BACKGROUND

The tripeptide hormone fragment Pro—L—Leu—Gly—NH$_2$, known as melanotrophic release-inhibiting hormone or MIF, has been reported as having pronounced effects on the central nervous system. For example MIF has been found to potentiate the behavioral effects of L-DOPA and apomorphine, attenuate puromycin-induced amnesia, and facilitate morphine dependence, thus suggesting that MIF should have activity against Parkinson's disease as well as have a "mood-elevating" effect. See Ehrensing et al, "Clinical Investigations for Emotional Effects of Neuropeptide Hormones," Pharmacol. Biochem. Behav., 5 (Suppl. 1), 89 (1976). Both of these actions have been supported by animal tests and clinical data. (For Parkinsonism, see Barbeau et al, "Double-blind Evaluation of Oral L-Prolyl-L-leucyl-glycine Amide in Parkinson's Disease," Can. Med. J., 114, 120 (1976), and for depression see Ehrensing et al, "Dose-Related Biphasic Effect of Prolyl-Leucyl Glycinamide (MIF-I) in Depression," Am. J. Psychiatry, 135, 562 (1978).) Practical use of MIF has been hindered, however, because MIF is rapidly cleaved by enzymatic action, and thus its half-life is very short. As a consequence, to enable significant effects to be obtained over a useful time period, it is necessary to administer large doses of MIF by intravenous infusion over long periods of time.

Because of this difficulty, attempts have been made to synthesize MIF analogs which will possess the same pharmacologic activity as MIF, but will be less susceptible to inactivation by enzymatic cleavage. For example, Voith, in "Synthetic MIF Analogues Part II: Dopa Potentiation and Fluphenazine Antagonism," Arzneimittel-Forsch., 27, 2290 (1977), reports efforts to improve effective MIF life by introducing a methyl substituent on the amino group of the central leucine (Leu) peptide, the use of the N-methyl-D-Leu stereoisomeric peptide, and the replacement of the 3-glycine (Gly) residue with D-alanine (D-Ala). However, such compounds were reported to have low potencies as compared with the parent MIF.

Another effort, reported by Bjorkman et al in "Tripeptide Analogues of Melanocyte-Stimulating Hormone Release-Inhibiting Hormone (Pro—Leu—Gly—NH$_2$) as Inhibitors of Oxotremorine-Induced Tremor", J. Med. Chem., 22, 931 (1979), involved replacement of the proline residue (Pro) by the pyroglutamic acid residue (pGlu), and the alkylation of the terminal amide group of the Gly—NH$_2$ residue. The reported data indicate that the activities of the resulting analogs against oxotremorine-induced tremor ranged from nil to significant increases in potency as compared to the parent MIF. No data were presented with respect to half-life of these agents. Furthermore, since these compounds were injected i.p., and thus may have been severely degraded through enzymatic degradation in the liver before reaching the brain, the post-hepatic dosage of these materials, and thus their true activity, is presently unknown.

OBJECTS OF THE INVENTION

It is an object of the present invention to provide new MIF analogs having effects on the central nervous system.

It is a further object of this invention to provide MIF analogs having enhanced potency and half-life.

Still another object of the invention is the provision of MIF analogs having improved resistance to enzymatic degradation.

A still further object of the invention is the provision of MIF analogs which are sufficiently stable to enable oral administration.

Yet another object of the invention is the provision of a method for affecting the central nervous system by oral administration of certain MIF analogs.

SUMMARY OF THE INVENTION

In accordance with this invention, new analogs of MIF characterized by increased potency and half-life are provided. These analogs are characterized by replacement of the L-Leu peptide by its D-Leu stereoisomer. Optionally, the Pro peptide may be replaced by pGlu and the terminal amide group may contain one or two lower alkyl groups. These MIF analogs may be represented by the formula:

$$X\text{—D—Leu—NH—CH}_2\text{—CONR}^1\text{R}^2 \qquad (I)$$

wherein X is Pro or pGlu and each of R$^1$ and R$^2$, when taken separately, is hydrogen or lower alkyl, especially methyl or ethyl. Such analogs have been found to be highly resistant to enzymatic cleavage, and thus they may be administered orally.

Of the compounds illustrated by the above formula, that where X is Pro and R$^1$ and R$^2$ each are hydrogen is a known compound, it having been synthesized by Schneider et al (J. Am. Chem. Soc., 84, 3005 (1962)) as an intermediate for the synthesis of [8-D-Leu]-oxytocin. However, this substance was not tested as a pharmaceutically active material. Consequently, the novel compounds with which this invention is concerned may be represented by the formulae:

$$\text{Pro—D—Leu—Gly—NRR}^1 \qquad (II)$$

wherein R is lower alkyl and R$^1$ is hydrogen or lower alkyl; and $$\text{pGlu—D—Leu—Gly—NR}^1\text{R}^2 \qquad (III)$$

wherein R$^1$ and R$^2$ are as previously defined.

The MIF analogs with which this invention is concerned are readily prepared by conventional procedures for the step-wise synthesis of polypeptides, including solid phase syntheses of the type described generally by Stewart et al, "Solid Phase Peptide Synthesis," W. H. Freeman & Co., San Francisco (1969).

The following examples illustrate the synthesis of MIF analogs within the scope of Formula (I), above.

EXAMPLE I pGlu—D—Leu—Gly—NH$_2$ (a) Carbobenzoxy-D-leucine (7.96 g, 30 mMol), and 1-hydroxybenzotriazole monohydrate (4.46 g, 33 mMol) were dissolved in dimethylformamide (50 ml), the solution was chilled with ice and dicyclohexylcarbodiimide (6.18 g, 30 mMol) was added. After stirring the solution for one hour, Gly—OEt—HCl (4.18 g, 3 mMol) and triethylamine (4.20 ml, 30 mMol) were added and the ice bath was removed. The mixture was stirred for 6 hours at room temperature, chilled for 24 hours and filtered. The filtrate was concentrated in vacuo, dissolved in 75 ml ethyl acetate, and extracted with three 50 ml portions of 5% sodium bicarbonate. The organic phase was dried over sodium sulfate and concentrated to an oil. The residue was crystallized from aqueous ethanol to yield 10.5 g of carbobenzoxy-D-Leu-Gly; ethyl ester (100% yield). Melting point 100°–101° C. On TLC only a single spot could be observed.

(b) A 2.0 g (5.69 mMol) portion of this ester was hydrogenated for 3 hours in absolute ethanol at atmospheric pressure using 10% Pd on charcoal as a catalyst. The solution was filtered and evaporated to dryness. The resulting material was coupled with N-(tert-butyloxycarbonyl)-pGlu (1.30 g, 5.69 mMol) in dimethylformamide (10 ml) by means of dicyclohexylcarbodiimide (1.17 g, 5.69 mMol), hydroxybenzotriazole monohydrate (0.923 g, 6.83 mMol) and triethylamine (0.8 ml, 5.69 mMol), employing procedures similar to those described above. After evaporation of the dimethylformamide, the residue was dissolved in 50 ml ethyl acetate and was extracted three times with 30 ml portions of 5% sodium bicarbonate, three times with 30 ml portions of water and three times with 30 ml portions of 0.01 M HCl. The organic phase was dried over sodium sulfate and concentrated to an oil. The residue was crystallized from ethyl acetate-hexane to yield 870 mg (38%) of N-(tert-butyloxycarbonyl)-pGlu-D-Leu-Gly, ethyl ester, which was homogenous on TLC.

(c) A 100 mg portion of the tripeptide ester was treated with trifluoroacetic acid for 30 minutes. The solution was evaporated to dryness, 30 ml toluene were added, and the solution was again evaporated to dryness. The toluene treatment was repeated two more times. The residue was crystallized from ethyl acetate-heptane to yield 54 mg (73%) of pGlu—D—Leu—Gly, ethyl ester as a product homogenous on TLC. Amino acid analysis: Leu 1.1, Glu 0.9, Gly 0.9.

(d) A 150 mg portion of this product was dissolved in 100 ml and the resulting solution was saturated with dry ammonia gas (freshly distilled over sodium). After three days at room temperature, the solution was concentrated in vacuo and the residue was crystallized from ethanol-ether to yield 70 mg (47%) of pGlu—D—Leu—Gly—NH$_2$, which was homogenous on TLC. Amino acid analysis: Leu 1.1, Glu 0.9, Gly 0.9.

EXAMPLE II pGlu—D—Leu—Gly—NHCH$_3$

The p—Glu—D—Leu—Gly, ethyl ester produced as described in step (c) of Example I is dissolved in methyl amine, and the mixture is stirred to yield p—Glu—D—Leu—Gly—NHMe. Other alkylamides, such as the ethyl amide, the dimethyl amide, the isopropyl amide, and the like, are obtained by substituting the appropriate amine (i.e., ethylamine, dimethyl amine, isopropylamine, and the like) for methyl amine.

EXAMPLE III

Pro—D—Leu—Gly—NH$_2$

Employing procedures described by Schneider et al, 84, 3005 (1962), Pro—D—Leu—Gly—NH$_2$ was prepared in 97% yield. Amino acid analysis: Pro 1.0, Leu 0.9, Gly 0.9.

EXAMPLE IV

Pro—D—Leu—Gly—NHCH$_3$

Employing procedures similar to those described in Example I, except that N—t—Boc—Pro is substituted for N—t—Boc—pGlu, Pro—D—Leu—Gly, ethyl ester is produced. The ester is then reacted with methyl amine as described in Example II to yield Pro—D—Leu—Gly—NHCH$_3$.

As has been noted above, the MIF analogs of Formula (I) all have pronounced effects on the central nervous system, and thus are useful in the treatment of Parkinson's disease, depression and other disorders associated with the central nervous system. Because of the presence of the D-Leu residue at position 2, these compounds all resist enzymatic cleavage, and hence have long half-lives when administered to mammals. Furthermore, their stability is such that their administration may be in an oral dosage form.

The MIF analogs were tested for "Parkinsonion" locomotor behavior response by three different test procedures.

In the first series of tests, male Long-Evans rats were prepared with a cannula fixed from the exterior to the lateral ventricle for direct intraventricular administration. The rats were reserpinized i.p. (10 mg/kg), and then MIF or MIF analogs, were given directly into the CSF. Activity of the rats was measured in counts/10 minutes with a digital printout activity meter (Columbus Instruments, model PB 5244, Columbus, Ohio). The results of these tests are as follows

| Agent | % Increase in Activity, Counts/10 Minutes | |
|---|---|---|
| | 10 ng. | 100 ng. |
| MIF | No effect | No effect |
| pGlu—D—Leu—Gly—NH$_2$ (Example I) | 240 | 360 |
| Pro—D—Leu—Gly—NH$_2$ (Example II) | 120 | 230 |

From the foregoing, it is evident that both D-Leu derivatives were active, whereas the parent MIF, was without significant activity. Furthermore, the novel pGlu derivative of this invention was significantly more active than the known Pro derivative.

In the second series of tests, male Long-Evans rats prepared and reserpinized as described for the first series, were treated i.p. with 2 mg/kg of MIF or MIF analog, 10 mg/kg of Carbi-DOPA, a competitive inhibitor of DOPA-decarboxylase (to prolong the L-DOPA effect), and 100 mg/kg of L-DOPA. The control group received the latter two substances, but no MIF or MIF analog. Activity of the rats was measured, in counts/10 minutes with a digital printout activity meter, at 15, 35, 55, 75, 95 and 105 minutes after injection. The results of this series of tests were:

| Agent | % Increase in Activity, counts/10 min. | | | | | |
| --- | --- | --- | --- | --- | --- | --- |
| | 15 min. | 35 min. | 55 min. | 75 min. | 95 min. | 105 min. |
| Control | −44 | 344 | 11 | 111 | 261 | 167 |
| pGlu—D—Leu—Gly—NH$_2$ (Example I) | 126 | 538 | 2450 | 2036 | 1035 | 478 |
| Pro—D—Leu—Gly—NH$_2$ (Example II) | 83 | 442 | 1383 | 1008 | 983 | 367 |

From the foregoing, it can be seen that both MIF analogs were active, but again the novel pGlu analog was more effective than the known Pro analog. It is also seen that both MIF analogs appear to have a peak activity approximately one hour after administration.

In the third series of tests, male Sprague-Dawley rats received a unilateral chemical lesion (by injection of 6-hydroxy-Dopamine) in the substantia nigra, which is followed by rotational movement. When L-DOPA is given i.p. (in two doses, 13 and 26 mg/kg) the direction of rotational movement is reversed, and the duration of the reversed rotational motion was measured in minutes. The same doses of L-DOPA were then given in the experimental groups in combination with 2 mg/kg of either MIF or the MIF analogs, all i.p., or by gastric tube in a dose of 4 mg/kg, and the duration, in minutes, of reversed rotational behavior was observed. The results are as follows:

| Agent | Duration of Reversed Rotational Behavior, min. | |
| --- | --- | --- |
| | Injection | Oral |
| L-DOPA | 38 ± 3.4 | 38 ± 3.4 |
| L-DOPA + MIF | 55 ± 6.2 | 58 ± 5.3 |
| L-DOPA + pGlu—D—Leu—Gly—NH$_2$ (Example I) | 96 ± 7.9 | 110 ± 9.3 |
| L-DOPA + Pro—D—Leu—Gly—NH$_2$ (Example II) | 74 ± 6.3 | 80 ± 8.2 |

As in the first two series of tests, the MIF analogs of this invention proved to be more active than the parent MIF, and the novel pGlu derivative of this invention proved to be more active than the known Pro analog.

The amount of the tripeptide MIF analog which is administered to the host will be dependent upon the effect being treated, the particular analog being used, and the tolerance and response of the specific host being treated. In general, however, the dosage will fall within the range of from about 1 to about 20 milligrams of the MIF analog per kilogram of body weight.

The agent can be administered by any convenient mode of administration, as by intravenous or subcutaneous injection, or in an oral dosage form. Injectable dosage forms typically comprise an aqueous solution of an analog of Formula (I), above. Such a solution may contain various additives generally known to the art. A preferred medium is physiological saline solution, which preferably is acidic, having a pH of from about 3 to about 5, and preferably about 4.

It is an advantage of the MIF analogs of Formula (I), above, that they can be administered orally. For such use, they can be incorporated into capsules, tablets or "syrups" suitable for oral consumption. Such oral dosage forms will include a pharmaceutically acceptable, edible diluent, which is a solvent (e.g., water) for the MIF analog in the case of a liquid oral dosage form, or an inert pulverulent solid in the case of a tablet or capsule oral dosage form. Suitable diluents are well known to the art, and no useful purpose will be served by listing them here. Suffice it to say that various methods of formulating oral medicaments are disclosed in Remington's Pharmaceutical Sciences, Ed. Osol et al, 14th Ed., Mack Publ. Co.

Typical examples of oral dosage forms include capsules comprising a mixture of dry lyophilized tripeptide of Formula (I), above and mannitol as a diluent. The relative proportions tripeptide and diluent are not critical; however, it is preferred that there be from about 1 to about 10 mg. of dry lyophilized tripeptide in each capsule.

As another example of a suitable dosage form, the tripeptide of Formula (I) may be included into a tablet dosage form by mixing the tripeptide with a suitable binder (typically starch), and a lubricant, for example magnesium stearate, and compressing the mixture into tablets using dry granulation or direct compression techniques. The tablets may be colored through use of dyes, or through use of colored sugar coatings. Although not necessary, the tablets may be provided with enteric coatings, or be formulated as chewable tablets, and the like, should this be desired. As was the case with capsules, the tablet desirably contains from about 1 to about 10 mg of the MIF analog.

What is claimed is:

1. A tripeptide represented by the general formula:

X—D—Leu—Gly—NR$^1$R$^2$ wherein X is the proline (Pro) or pyroglutamic acid (pGlu) residue, D-Leu is the D-leucine residue, Gly is the glycine residue, and each of R$^1$ and R$^2$, when taken separately, is hydrogen or lower alkyl with the proviso that when X is proline, R$^2$ is lower alkyl.

2. A tripeptide according to claim 1 wherein each of R$^1$ and R$^2$ is hydrogen, methyl or ethyl.

3. A tripeptide according to claim 2 wherein X is Pro.

4. A tripeptide according to claim 2 wherein X is pGlu.

5. A tripeptide according to claim 4 wherein R$^1$ and R$^2$ are hydrogen.

* * * * *